United States Patent [19]

Deits

[11] Patent Number: 5,766,914
[45] Date of Patent: Jun. 16, 1998

[54] METHOD OF PRODUCING AND PURIFYING ENZYMES

[75] Inventor: Thomas L. Deits, Williamston, Mich.

[73] Assignee: Michigan State University, East Lansing, Mich.

[21] Appl. No.: 378,698

[22] Filed: Jan. 26, 1995

[51] Int. Cl.$^6$ .............................. C12N 9/38; C12P 21/04; A23J 1/00; C07H 21/04
[52] U.S. Cl. .................. 435/207; 435/69.7; 530/412; 536/23.4
[58] Field of Search ........................ 435/207, 69.7; 530/412; 536/23.4

[56] References Cited

U.S. PATENT DOCUMENTS

| | | | |
|---|---|---|---|
| 5,081,034 | 1/1992 | Bevilacqua et al. | 435/252.33 |
| 5,179,007 | 1/1993 | Jarvis et al. | 435/68.1 |
| 5,223,394 | 6/1993 | Wallner | 435/6 |
| 5,223,409 | 6/1993 | Ladner et al. | 435/69.7 |
| 5,348,867 | 9/1994 | Georgiou et al. | 435/69.7 |

FOREIGN PATENT DOCUMENTS

WO 91/17271  11/1991  WIPO.

OTHER PUBLICATIONS

Schoel et al. (1988) J. Chromatography 448: 165–172.
William Donovan et al., "Genes Encoding Spore Coat Polypeptides from *Bacillus subtilis*", J. Mol. Biol. (1987) 196, pp. 1–10.
Liangbiao Zhend et al., "Cascade Regulation of Spore Coat Gene Expression in *Bacillus subtilis*", J. Mol. Biol. (1990) 212 pp. 645–660.
Joseph A. Francisco et al., "Production and fluorescence–activated cell sorting of *Escherichia coli* expressing a functional antibody fragment on the external surface", Proc. Natl. Acad. Sci. USA vol. 90, pp. 10444–10448, Nov. 1993, Biochemistry.
Joseph A. Francisco et al., "Specific Adhesion and Hydrolysis of Cellulose by Intact *Echericha coli* Expressing Surface Anchored Cellulase or Cellulose Binding Domains", Bio./Technology vol. 11, Apr., 1993, pp. 491–495.
Adam Driks et al., "Subcellular localization of proteins involved in the assembly of the spore coat of *Bacillus subtilis*" Genes & Development, 1994 8, pp. 234–244.

Primary Examiner—Robert A. Wax
Assistant Examiner—Lisa J. Hobbs
Attorney, Agent, or Firm—Quarles & Brady

[57] ABSTRACT

A method of producing and purifying an enzyme which comprises selecting a spore forming host organism, preparing a genetic construct consisting of a DNA sequence encoding the desired enzyme and a DNA sequence directing synthesis of the desired enzyme during sporulation, inserting the genetic construct into the host organism, culturing the transformed host organism under sporulating conditions to obtain host organism spores with the enzyme integrally associated to the spores, and then treating the host organism and enzyme combination to remove any impurities, if necessary. The free enzyme can be obtained by cleaving the connection between the host organism and the enzyme. The combination of the enzyme and host organism is both a stabilized and an immobilized enzyme preparation.

5 Claims, 6 Drawing Sheets

METHOD OF PRODUCING AND PURIFYING ENZYMES

FIELD OF THE INVENTION

The present invention relates generally to enzymes. More particularly, it relates to the production and purification of enzymes.

BACKGROUND OF THE INVENTION

A number of valuable enzymes are currently produced only intracellularly, presenting significant purification problems. Most of these enzymes currently can only be produced in a purified form, free of cellular and other detrimental materials, by use of lengthy and costly procedures. It would be advantageous to be able to produce such enzymes in a purified form by a simple method.

There also are a significant number of intracellular and extracellular enzymes that are not currently available in stabilized forms, and there are a number of enzymes that would be more useful if they were immobilized on a nontoxic biodegradable support. It would be advantageous to be able to produce enzymes in a stabilized form or immobilized on a non-toxic biodegradable support.

BRIEF SUMMARY OF THE INVENTION

The method of the present invention comprises selecting a spore-forming host organism, forming a genetic construct comprising a first DNA sequence encoding a desired enzyme and a second DNA sequence directing synthesis of the desired enzyme during sporulation. The host organism is then transformed with the genetic construct and cultured under sporulating conditions so that the desired enzyme is produced in a form which is integrally associated with the mature spore, thus making it possible to remove undesired impurities from the spore-enzyme combination by methods for the purification of spores known to those skilled in the art.

In a preferred form of the invention, the construct comprises a DNA sequence encoding a spore coat protein which, when transcribed and translated, expresses a fusion protein between the spore coat protein and the target enzyme. This spore coat protein will preferably form part of the spore coat of the wild type organism and provide a means whereby the desired enzyme may be integrally associated with the spore coat of the transformed organism.

In a preferred form of the present invention, the enzyme is an active form. By "active form" we mean that on average, each spore expresses enzyme activity equivalent to the activity of at least $1 \times 10^3$ molecules, and preferably at least $1 \times 10^4$ molecules, of the native enzyme.

If it is desired to isolate the enzyme from the spore of the host organism, the fusion protein between the spore coat protein and the target enzyme can be cleaved, as by use of a protease, or acid treatment or other known methods, to obtain the enzyme separated from the spore coat.

The spore of the host organism with the enzyme integrally associated thereto is a preferred stable form of the enzyme and can be used as an immobilized form of the enzyme.

It is an object of the present invention to provide a simple, novel method of producing and purifying enzymes.

It also is an object to produce intracellular enzymes extracellularly so that the enzymes can be more simply purified.

Further objects are to disclose a novel method of producing stabilized enzymes and the stabilized enzymes thus produced.

Still further objects are to disclose a method of producing enzymes immobilized on a non-toxic biodegradable support and the immobilized enzymes thus produced.

It will be apparent to those skilled in the art that other objects, advantages and features will become apparent after review of the specification, claims and figures presented herein.

DESCRIPTION OF THE DRAWINGS

FIG. 1A diagrams the light scattering properties of PY79 spores with intact coats in the absence or presence of lysozyme and decoated PY79 spores in the absence or presence of lysozyme. FIG. 1B diagrams the light scattering properties of spores of the cotC-lacZ fusion strain in the absence or presence of lysozyme and decoated cotC-lacZ fusion strain in the absence or presence of lysozyme.

DESCRIPTION OF PREFERRED EMBODIMENT

Figure 1A:
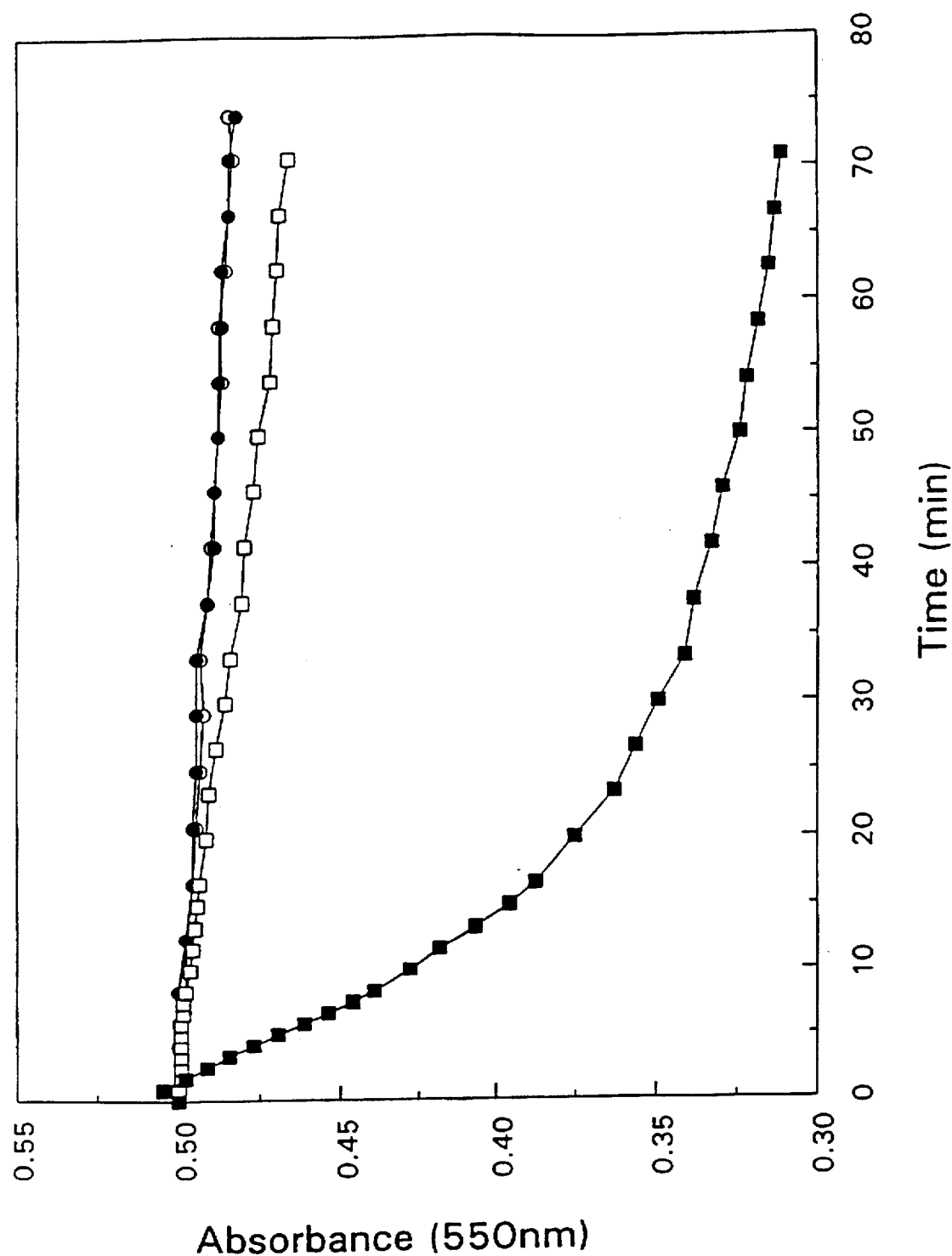
FIGS. 1A and 1B diagrams of lysozyme sensitivity of spores from strains PY79 and the cotC-lacZ fusion strain.

Especially preferred as a host organism for non-glycosylated enzymes that normally are produced by their parent organism intracellularly are spore forming strains of *Bacillus subtilis*. *B. subtilis* is a nonpathogenic, GRAS (Generally Recognized As Safe) organism which forms spores when cultured at about 36° C. to about 38° C. in the presence of an assimilable source of carbon and nitrogen and other minerals in a nutrient medium that will support growth (described in detail below).

The spore coat of *B. subtilis* is the outermost protective layer of the spore. It is composed more than a dozen proteins (J. Errington, *Microbiol. Rev.* 57:1–33, 1993). A number of the genes encoding proteins comprising the spore coat have been cloned by reverse genetic techniques in which proteins are extracted from the spore coat, purified, sequenced, and the gene cloned using the deduced nucleotide sequence of the protein.

At present, the coat genes cotA, cotB, cotC, cotD (W. Donovan, et al., *J. Mol. Biol.* 196:1–10, 1987), cotE (L. Zheng, et al., *Genes & Develop.* 2:1047–1054, 1988), cotF (S. Cutting, et al., *J. Bacteriol.* 173:2915–2919, 1991), cotT (A. Aronson, et al., *Mol. Microbiol.* 3:437–444, 1989), cotW, cotX, cotY and cotZ (J. Zhang, et al., *J. Bacteriol.* 175:3757–3766, 1993) have been cloned and at least partially sequenced. (The articles cited in this paragraph have been incorporated by reference as if fully set forth herein.) The sequences and amino acid compositions of the genes and proteins are highly diverse, testifying to the intricacy of this macromolecular assembly process.

Fusions to spore coat genes have proven to be a tool for the study of the genetic regulation of this complex developmental process (P. Youngman, et al., *Science* 228:285–291, 1985). These fusions consist of the promoter region of the gene of interest, a short stretch of the coding sequence of the spore coat gene, and, fused in frame, lacZ, the gene encoding β-galactosidase. The construct is then reintroduced into the *B. subtilis* chromosome, and the resultant strain is induced to sporulate. The measured level of β-galactosidase catalytic activity serves as a reporter for the level of gene expression of the original spore coat gene.

We have discovered that the products of cotC-lacZ and cotD-lacZ fusions are efficiently directed to the spore coat. The mature engineered spores bear β-galactosidase as a stable and catalytically active component of an otherwise intact spore coat. This observation allows us to predict that other combinations of enzymes and spore coat proteins and/or suitable promoters will be effective to produce a suitable association between the spore and the desired enzyme. The present invention comprises enzymes that are integrally associated with the spore coat. By "integrally associated" we mean that the enzyme forms an integral part of the spore coat. The enzyme may be entrapped in a matrix of spore coat proteins, may become cross-linked to existing sporulation proteins, or may become integrally associated by virtue of its covalent attachment as a fusion protein to a spore coat protein. A combination of these or other mechanisms which would be apparent to those skilled in the art may act to render the target enzyme integrally associated.

An enzyme is integrally associated with a spore coat if the enzyme activity cannot easily be separated from the spore. For example, the Examples below disclose purified transgenic spores which are retained on a filter substrate (which itself does not retain the soluble form of the target enzyme) and are subjected to a flow through the filter of a solution conducive to stability of the soluble target enzyme will lose less than 10% of the activity that would be lost if the soluble target enzyme were treated under the same conditions for the same period of time which, in the Example, is 24 hours. Spore-associated enzymes of the present invention will be at least as firmly associated with the host spore.

To practice the present invention, one must form a genetic construct encoding a desired enzyme. This construct must contain DNA sequences sufficient to promote expression of the desired enzyme during the process of sporulation. The Examples below demonstrate a preferred way of linking the promoter associated with the cotC gene, a DNA sequence encoding a portion of the cotC gene, and the lacZ gene arranged so that the gene product, a translational fusion of the proteins encoded by the cotC and lacZ genes, is appropriately expressed. One skilled in the art of molecular biology would realize that there are many suitable variations.

Briefly, one must link a promoter which can be made active in the host organism during the process of sporulation with a DNA sequence encoding the enzyme of interest. This genetic construct must be used to transform the host organism. By "transform" we mean that the host organism will undergo a genetic change following incorporation of new DNA. This transformation process is most typically performed by either of two methods employed by those skilled in the art. In the first method, the construct is inserted in a plasmid which is not viable (cannot replicate) in *B. subtilis* and which bears a marker selectable in *B. subtilis* (antibiotic resistance, for example). A host strain of *B. subtilis* is rendered competent for transformation by either electroporation or chemical treatment (C. R. Harwood, et al., "Molecular Biological Methods for Bacillus," John Wiley & Sons, New York, p. 33, 1990) and is treated with the plasmid. The transformed *B. subtilis* are selected for antibiotic resistance. Only those bacteria which integrate the construct via homologous (Campbell-type) recombination will be able to express the antibiotic resistance gene and survive. These bacteria will then have the desired construct stably integrated into their genome (C. R. Harwood, et al., supra, pp. 228–230).

Alternatively, a specialized transducing bacteriophage SPβ can be employed. In this approach, the construct is inserted in the phage and the host strain is infected with the phage. The bacteriophage then integrates at a site homologous to the host DNA it carries. Selection is accomplished by an antibiotic resistance marker on the phage (C. R. Harwood, et al., supra, pp. 56–58).

Any strain of *B. subtilis* that can be made competent for transformation and can form spores is suitable for the present invention. Representative of the strains of *B. subtilis* that can be used in the method are strain PY79 (W. Donovan, et al., *J. Mol. Biol.* 196:1–10, 1987); strains 4670 and 4673 (S. Nakashio, et al., *J. Bact.* 162:571–578, 1985); and strain ATCC 6051 (T. Koshikawa, et al., *J. Gen. Microb.* 135:2717–2722, 1989).

Representative of the DNA sequences of spore coat proteins which can be used with *B. subtilis* as the host organism are the sequences for the cotC gene (Donovan, et al., *J. Mol. Biol.* 196:1–10, 1987) and the cotD gene (Donovan, supra). These sequences are described below at SEQ ID NOs:1 and 2.

Representative of the enzymes which can be produced extracellularly by use of *B. subtilis* as the host organism are monomeric enzymes, such as carbonic anhydrase; dimeric enzymes, such as luciferase; monomeric fusions of dimeric enzymes, such as luciferase, trimeric enzymes, such as triose phosphate isomerase; and tetrameric enzyme and higher enzyme oligomers, such as aspartate transcarbamylase. Functional classes that could be produced extracellularly include hydrolases, such as phosphodiesterases; transferases, such as phosphorylases; oxidoreductases, such as peroxidases; and isomerases, such as triose phosphate isomerase. Other examples of both structural and functional classes of enzymes that could be produced using the method would be apparent to one skilled in the field.

In a preferred form of the present invention, the enzyme is an active form. By "active form" we mean that on average, each spore expresses enzyme activity equivalent to the activity of at least $1\times10^3$, and preferably $1\times10^4$, molecules of the native enzyme.

Glycosylated enzymes cannot be produced by the method of the present invention using *B. subtilis*. In order to produce the glycosylated enzymes it is necessary to use an organism, such as yeast, that is capable of producing a glycosylated gene expression product.

Representative of the yeast strains that can be used in the method of the present invention are the following: Strain PB2-1C (Briza, et al., *Genes and Development* 4:1775–1787, 1990); and strain AP3 (Briza, et al., *J. Biol. Chem.* 265:15118–1513, 1990).

When yeast is the host organism, the preferred second DNA segment is dit1 gene from *Saccharomyces cerevisiae* (P. Briza, et al., *Genes Dev.* 4:1775–1789, 1990), the DNA sequence of which is described below at SEQ ID NO:3.

Representative of other DNA segments encoding for spore coat proteins suitable for the present invention are the following: The dit2 gene from *Saccharomyces cerevisiae* (P. Briza, et al., *Genes Dev.* 4:1775–1789, 1990).

Representative of glycosylated enzymes that can be produced and purified by the practice of the present invention are glucose oxidase (A. de-Baetselier, et al., *J. Biotechnol.*

24:141–148 (1992)); mono-and diacylglycerol lipase (S. Yamaguchi, et al., *Biosci., Biotechnol., Biochem.* 56:315–199 (1992); and beta-glucanase (O. Olsen, et al., *J. Gen. Microb.* 137:579–585 (1991).

In the preferred practice of the present invention, impurities are removed from the combination of spore and enzyme. By "impurities" we mean molecules that would adversely affect the activity of the enzyme. Examples of impurities that are preferably removed include soluble constituents of the culture medium; soluble proteins and other compounds secreted by *B. subtilis* during the course of growth and sporulation; soluble proteins and other compounds which comprise the remnant of the mother cells in which the spores were produced; and insoluble material which is not pelleted by centrifugation for 30 sec. to 1 minute at 10,000–12,000×g.

A preferable manner of removing undesired impurities from the spore/enzyme combination is to simply wash the combination with distilled water or an appropriate aqueous solution.

In one embodiment of the present invention, the active enzyme is separated from the purified spore-enzyme combination. Representative of cleaving agents which can be used to isolate the active enzyme from the sporulated cells are proteases, mild acid treatment, and hydroxylamine treatment (T. E. Creighton, "Proteins, 2nd Edition" W. H. Freeman, New York, pp. 38–40, 1993). The choice of treatment will depend on the properties of the desired enzyme. Especially preferred are cleaving agents which do not disrupt the enzyme's activity or stability.

The spore forming host organism with the enzyme attached to the spore coat can be a more stable form of the enzyme than the enzyme per se. It also can be a biodegradable form of immobilized enzyme.

In the preferred practice of the method of the present invention, the genetic construct is formed from a DNA sequence obtained from *Escherichia coli* (J. Errington, *J. Gen. Microbiol.* 132:2953–2966, 1986) which encodes the enzyme β-galactosidase and the cotC DNA sequence obtained from *B. subtilis*, strain PY 17 (W. Donovan, et al., *J. Mol. Biol.* 196:1–10, 1987) which encodes for the spore coat protein CotC.

The genetic construct is then inserted into the DNA of the *B. subtilis* by either of the two methods described above.

The transformed *B. subtilis* is preferably cultured at about 36° C.–38° C. in the presence of an assimilable source of carbon and nitrogen and other minerals in a nutrient medium that will support growth and sporulation, such as Difco sporulation medium, which consists of 8 grams per liter medium Bacto-nutrient broth (Sigma Chemical Co., Catalog #N-7519 or equivalent from other suppliers) and 0.1% KCl, 0.012% $MgSO_4$, 0.005M NaOH, 0.001M $CaNO_3$, and $1\times10^{-6}$M $FeSO_4$) (C. R. Harwood, et al., "Molecular Biological Methods for Bacillus," John Wiley & Sons, New York, p. 549, 1990).

Once the enzyme production by the spore-forming host is complete, the sporulated cells with the desired enzymes attached are washed to remove impurities and extraneous material to obtain a purified host spore and enzyme combination. If it is desired to have the enzyme isolated from the host organism, the enzyme is then cleaved from the sporulated cell by using a cleaving agent, such as a protease. The enzyme is then readily isolated from the cellular material by conventional techniques, e.g. filtering.

The practice of the present invention will be better understood from the examples which follow.

EXAMPLE 1

Materials and Methods

β-galactosidase assay. The assay is based on that of Sambrook, et al. (J. Sambrook, et al., "Molecular Cloning (A laboratory manual)", 2nd Ed. Cold Spring Harbor Laboratory Press, Cold Spring Harbor, New York, 1989) with minor modifications. The assay mixture contains 0.1M sodium phosphate, pH 7.5, containing 3 mM o-nitrophenyl β-D-galactopyranoside 6-phosphate (ONPG), 40.5 mM 2-mercaptoethanol and 90 μM $MgCl_2$ in a total volume of 600 μL. Reactions were initiated by addition of enzyme, and carried out at room temperature unless otherwise noted. Activity was determined from the slopes of initial rates monitored at 420 nm. O-nitrophenol, the product of β-galactosidase-catalyzed hydrolysis of ONPG, has a molar extinction coefficient at 420 nm under assay conditions of $3.1\times10^3$ $M^{-1}cm^{-1}$ (R. C. Weast, "Handbook of Chemistry and Physics", 60th ed. CRC Press, Boca Raton, Fla., 1979). β-galactosidase activity is reported in units of μmol ONPG hydrolyzed/min.

cot-lacZ fusions. Strains bearing the cotC-lacZ and cotD-lacZ fusions were generously provided by L. Kroos. (Department of Biochemistry, Michigan State University, East Lansing, Mich. 48824). These fusions were constructed and characterized previously (L. Zheng, et al., *J. Mol. Biol.* 212:645–660, 1990). The DNA sequence of cotC gene product and its associated upstream sequences (Genbank Accession number X05680), as inserted in the fusion protein are described at SEQ ID NO:1. The deduced amino acid sequence contributed by the cotC gene product to the cotC-lacZ fusion product begins at nucleotide 356 of the above DNA sequence and is described below at SEQ ID NO:4. SEQ ID NO:4 includes the initial methionine. The lacZ DNA sequence which comprises the fusion to cotC was constructed from the BamHI-BglII lacZ-cat cassette of plasmid pSGMU31 (J. Errington, *J. Gen. Microb.* 132:2953–2966, 1986). Plasmid pSGMU31 is in turn derived from plasmid pMC1871 (M. J. Casadaban, et al., *Adv. Enzymol.* 100:293–308, 1983) such that the coding sequences of cotC and lacZ are in-frame and are translated as a fusion protein. Those skilled in the art will recognize that many variations in the sequence comprising the region of lacZ to which the cotC sequence is fused could be employed.

The DNA sequence of cotD which is present in the cotD-lacZ fusion sequence (data from L. Zheng, et al., *J. Mol. Biol.* 212:645–660, 1990 and Genbank, Accession Number X05681) is described at SEQ ID NO:2. This sequence was blunt-end ligated to plasmid pLZ206 (L. Zheng, et al., supra) which was opened at its unique BamHI site and rendered blunt with Klenow fragment. Plasmid pLZ206 is a derivative of plasmid pSGMU31 (J. Errington, 1986, supra). Variant means of constructing the fusion to lacZ will be apparent to those skilled in the field (see, for example M. J. Casadaban, et al., supra).

The cotC-lacZ fusion includes 355 bp upstream of the open reading frame of cotC and 47 codons of the open reading frame fused in frame to lacZ from plasmid pSGMU31. The cotD-lacZ fusion includes 237 upstream bp and 58 codons of the open reading frame of cotD. The gene fusions were recombined into the SPβ prophage of *B. subtilis* strain ZB493 (available from L. Kroos, Dept. of Biochemistry, Michigan State University, E. Lansing, Mich. 48824, or from R. Losick, Dept. of Cellular and Developmental Biology, The Biological Laboratories, Harvard University, 16 Divinity Avenue, Cambridge Miss. 02138). Lysates of the resulting strains were then introduced into strain PY79 by specialized transduction (P. Youngman, et al., supra). Spores from the prototrophic strain PY79 (available from L. Kroos, Dept. of Biochemistry, Michigan State University, E. Lansing, Mich. 48824, or from R. Losick, Dept. of Cellular and Developmental Biology, The Biological Laboratories, Harvard University, 16 Divinity Avenue, Cambridge Miss. 02138) were employed as wild-type controls. Note that in both cases, the wild-type genes for cotC and cotD are present in the fusion strains.

Spore purification. A 10 L culture of sporulation medium (C. R. Harwood, et al., "Molecular Biological Methods for Bacillus," John Wiley & Sons, Inc. New York p. 549, 1990) was inoculated with 400 mL of exponentially growing bacteria, and permitted to grow at 37° C. with vigorous aeration and stirring until the medium was exhausted and no further growth was observed for 16 hours. Spores were collected by centrifugation, and washed twice with 2% Triton X-100, 0.2M NaCl, once with 0.2M NaCl, and three times with $H_2O$. Yields of ca. $1\times10^8$ spores/ml of medium were typical. The washed spore preparations were examined by light microscopy and consisted of uniformly sized highly refractile particles; the spores of cotC-lacZ and cotD-lacZ strains appeared identical to wild-type B. subtilis spores. No cell debris could be detected. Spore concentration was estimated from light scattering in $H_2O$ at 550 nm. An absorbance of 1.0 at 550 nm was taken as representing a concentration of $2\times10^8$ spores/mL.

Lysozyme sensitivity of spores. Spores were suspended in 0.1M potassium phosphate buffer, pH 7.5 at t=0. Lysozyme treatment consisted of the addition of 200 µg/ml lysozyme (Boehringer Mannheim) to the buffer prior to spore addition. Spore coats were removed by the SDS/DTT method (C. R. Harwood, et al., "Molecular Biological Methods for Bacillus," John Wiley & Sons, Inc. New York p. 442, 1990). $5\times10^9$ spores were centrifuged from their suspension and resuspended in 1 ml $H_2O$ containing 1% SDS and 50 mM DTT, prewarmed to 70° C. The suspension was incubated for 30 min. at 70° C. with occasional vortexing. Spores were then collected by centrifugation and washed by resuspension and centrifugation three times with $H_2O$, and finally resuspended in 0.1M potassium phosphate buffer, pH 7.5.

Flow reactor measurement of β-galactosidase in spores. $4\times10^8$ spores were injected on the upstream side of a 0.22 µm syringe filter (Millipore GS filter unit). The filter was inserted in line between an HPLC pump and a UV-vis detector (Waters, Inc.). β-galactosidase assay buffer was deaerated by repeated vacuum degassing and Ar purging prior to addition of 2-mercaptoethanol to ensure that adventitious oxidation would not occur during the course of the experiment. The buffer showed no significant absorbance at 420 nm either before or after the experimental run. Buffer was pumped through the syringe filter at 50 µL/min. beginning at t=0, and the absorbance at 420 nm was monitored.

EXAMPLE 2
Expression of Fusion Protein in B. Subtilis

When a suspension of $1.2\times10^8$ spores from the cotC-lacZ fusion strain was assayed for β-galactosidase activity, the observed rate of absorbance increase in the assay to 420 nm was 0.10 abs/min., equivalent to 0.02 units of β-galactosidase activity. The β-galactosidase activity of 1.2× $10^8$ spores bearing the cotD-lacZ fusion was 0.024 abs/min., 4-fold lower than the activity expressed by spores bearing the cotC-lacZ fusion. The measured activity was linear with volume of added spores, and the assays were linear with time, as is the case with native β-galactosidase. Wild-type B. subtilis spores did not exhibit detectable β-galactosidase activity. Although the spore suspension is turbid and has an appreciable absorbance at 550 nm due to light scattering, the light scattering properties of the sample did not change during the period of assay.

Stability of engineered spores. The CotC:β-galactosidase fusion was well integrated into the spore coat. When purified spores were subjected to 10 cycles of suspension in 0.1% Triton X-100 in $H_2O$ followed by centrifugation, less than 10% of the total activity initially present was lost from the spore pellet. Spores of both the cotC-lacZ and cotD-lacZ strains did not lose catalytic activity upon storage for several months at −20° C.

Figure 1B:
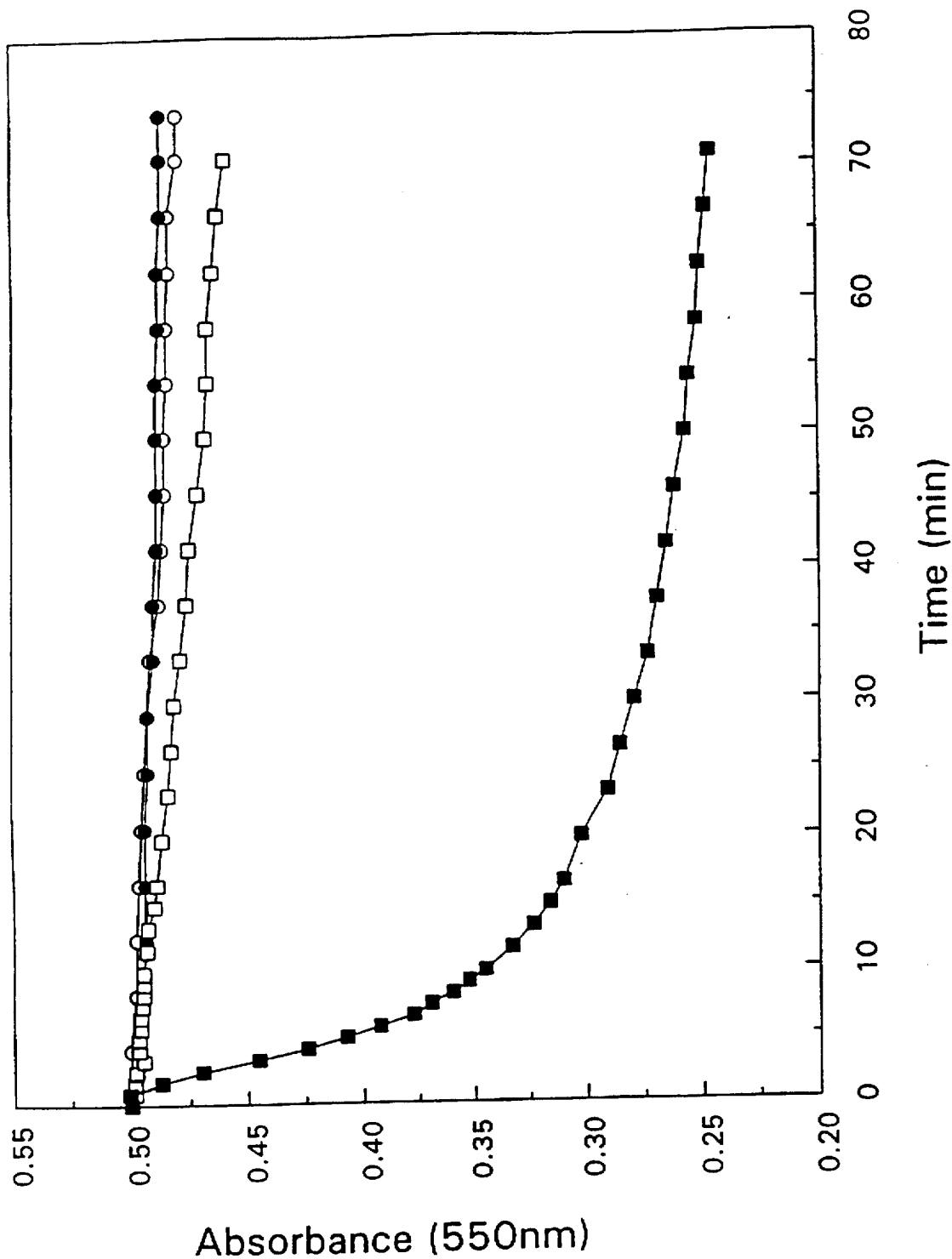

FIG. 1 diagrams the lysozyme sensitivity of spores from strains PY79 and the cotC-lacZ fusion strain. FIG. 1A diagrams the light scattering properties of PY79 spores with intact coats in the absence (○) or presence (●) of 200 µg/ml lysozyme, and decoated PY79 spores in the absence (□) or presence (■) of 200 µg/ml lysozyme. FIG. 1B diagrams light scattering properties of spores of the cotC-lacZ fusion strain. The symbols are the same as in FIG. 1A. Spore concentrations were adjusted to give ca. 0.5 absorbance units as the initial absorbance in each case. Data have been normalized to a common initial absorbance for clarity of comparison.

FIG. 1 demonstrates that spores of both PY79 and the strain bearing the cotC-lacZ fusion are resistant to lysozyme. When the spore coat is removed from either spore type, the spores become lysozyme sensitive.

Figure 2:
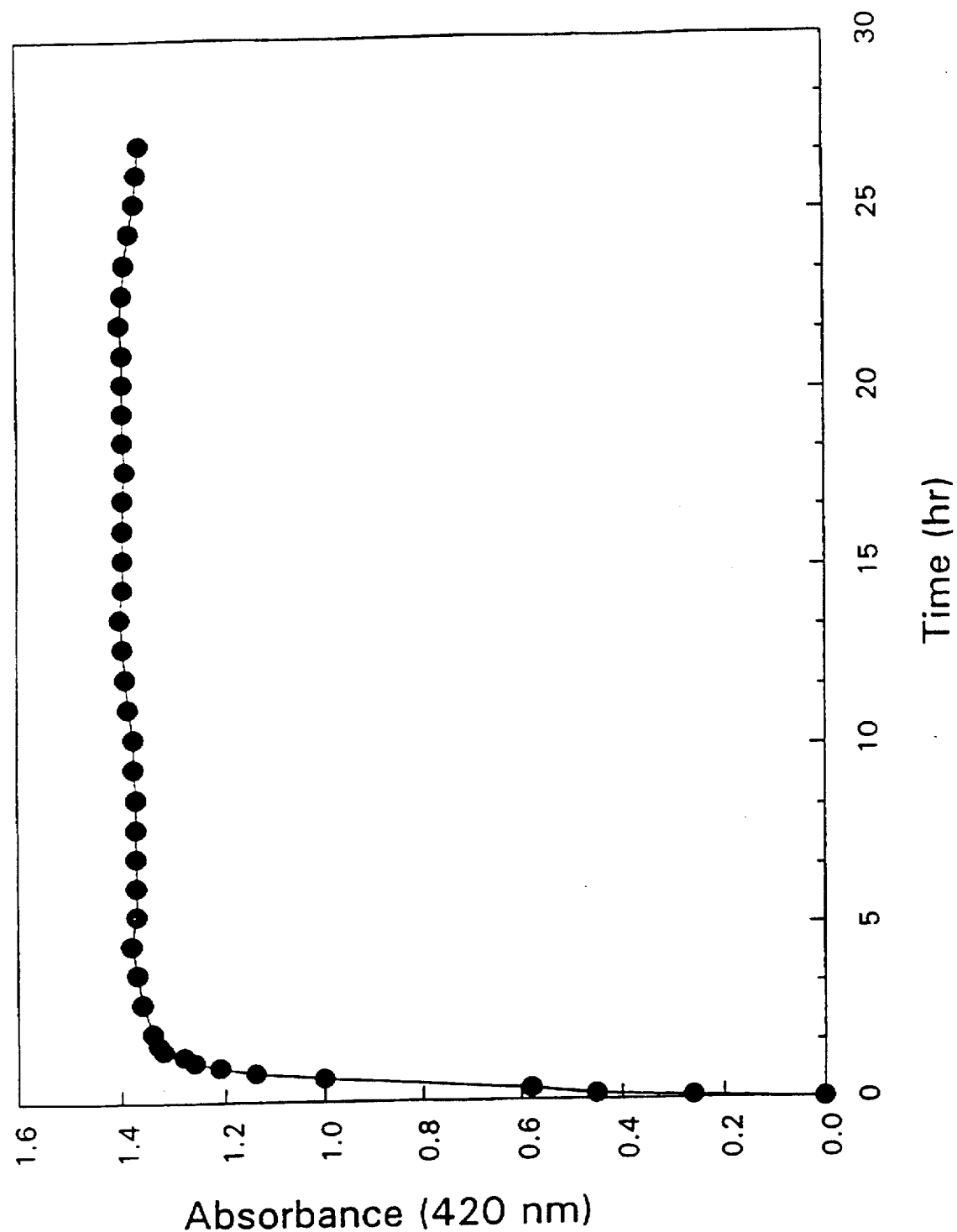
FIG. 2 is a graph of the stability of spores of the cotC-lacZ fusion strain under turnover conditions.

FIG. 2 diagrams the stability of spores of the cotC-lacZ fusion strain under turnover conditions. The operation of the flow reactor is described above. The measured absorbance values are directly proportional to the steady state velocity of catalysis by β-galactosidase at the indicated times.

FIG. 2 demonstrates the long-term stability of β-galactosidase immobilized in B. subtilis spore. Spore-immobilized β-galactosidase catalyzed ONPG hydrolysis with undiminished efficiency for more than 24 hours. Native β-galactosidase is not retained on these filters, so the enzyme must remain physically associated with intact spores throughout the course of this experiment.

The affinity of wild-type spores for β-galactosidase. The close association of the CotC:β-galactosidase fusion with the spore coat might occur through the normal pattern of spore coat deposition, or, alternatively, spores of B. subtilis might interact directly with β-galactosidase, in which case the observed immobilization would be due to an adventitious interaction between the enzyme and spore coat components.

We tested for interactions between wild type spores and β-galactosidase by mixing a quantity of native soluble β-galactosidase (equivalent to that found in ca. $1\times10^8$ spores from the cotC-lacZ fusion strain) with aliquots of from $2\times10^6$ to $7\times10^{10}$ wild-type B. subtilis spores, and then the spores were removed by centrifugation. There was not detectable loss of β-galactosidase activity from the supernatant. Sonicates of the cotC-lacZ fusion strain taken 8 hours after induction of sporulation by medium exhaustion contained appreciable quantities of soluble CotC:β-galactosidase fusion protein (L. Zheng, et al., supra, 1990). When PY79 spore suspensions were treated with this sonicate as was done for the purified enzyme, no β-galactosidase remained associated with the spores. Neither native β-galactosidase nor the CotC:β-galactosidase fusion protein exhibits appreciable affinity for mature wild-type spores.

Figure 3:
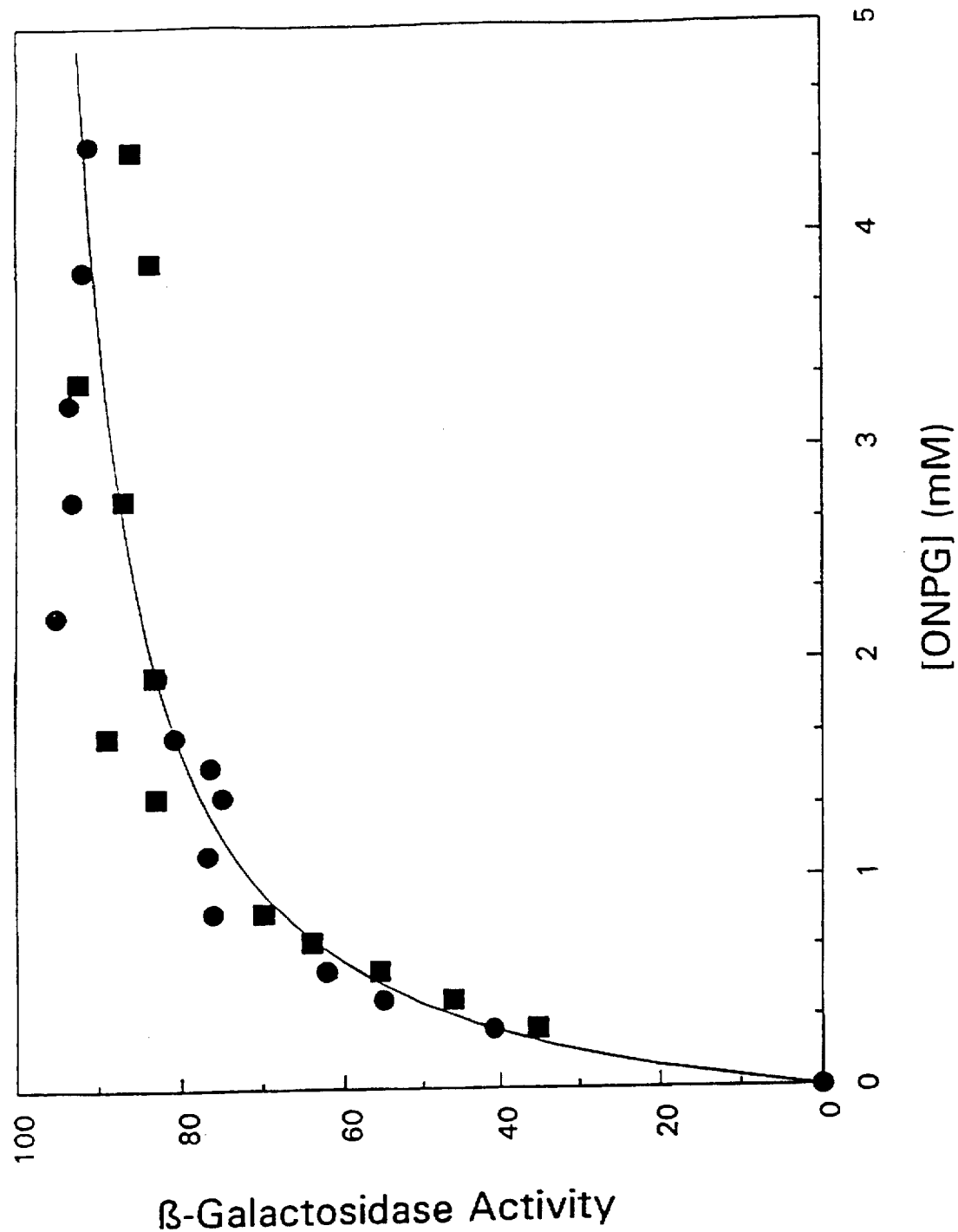
FIG. 3 is a graph of the $K_M$ values for native β-galactosidase and the CotC-β-galactosidase fusion in the spore coat of spores from the cotC-lacZ fusion strain.

Catalytic properties of β-galactosidase in the spore coat. FIG. 3 diagrams $K_M$ values for native β-galactosidase (●) and the CotC-β-galactosidase fusion in the spore coat of spores from the cotC-lacZ fusion strain (■). Data sets were normalized to the same $V_{max}$ value, set equal to 100. The smooth curve is a theoretical curve for an enzyme obeying the Michaelis-Menten equation $V_{obs}=V_{max}*[ONPG]/(K_M+[ONPG])$ with $V_{max}=100$ and $K_M=0.40$ mM. FIG. 3 shows that the $K_M$ values are essentially identical for native β-galactosidase and for the enzyme immobilized in the spore coat.

Figure 4:
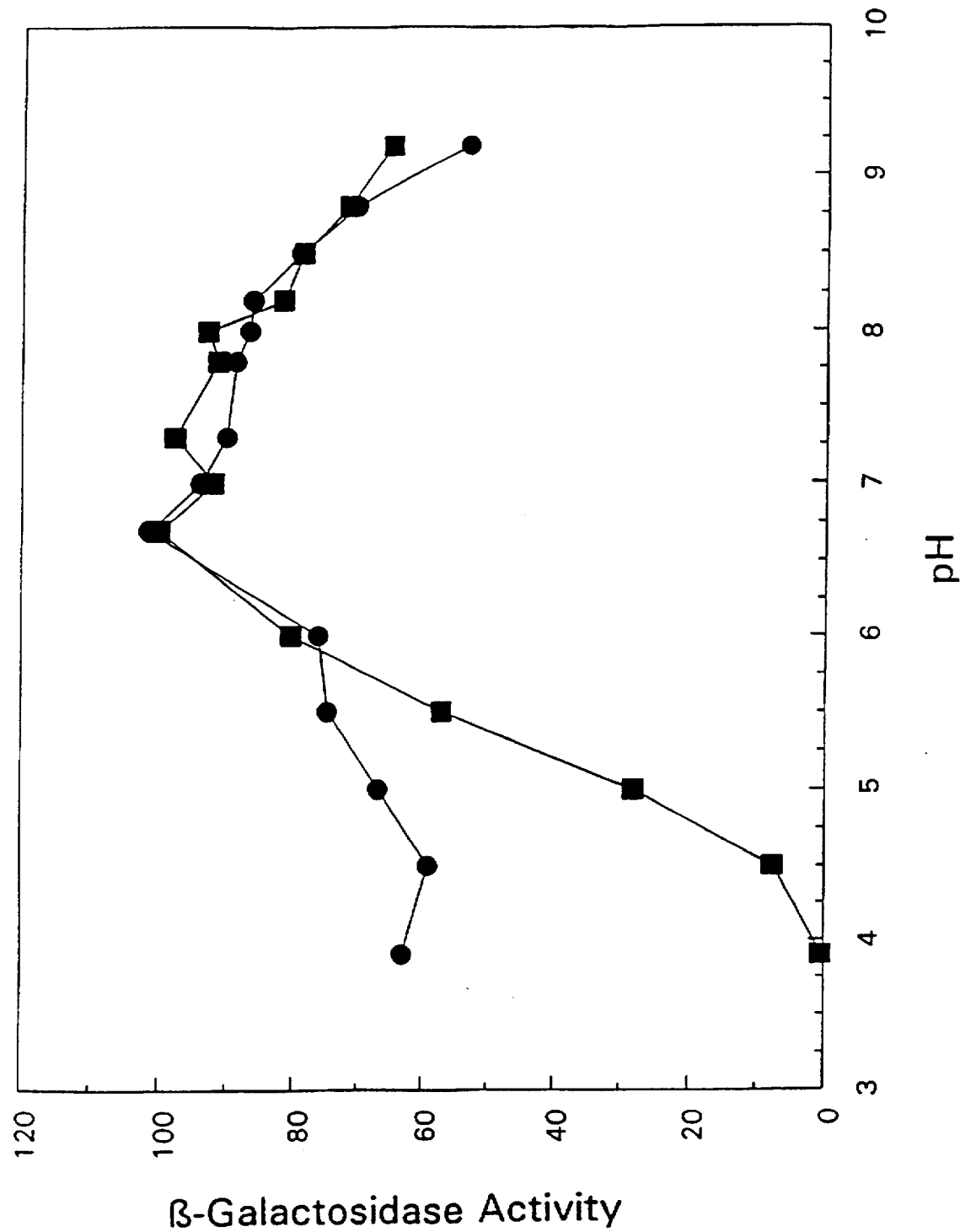
FIG. 4 is a pH activity profile for native β-galactosidase and the CotC-β-galactosidase fusion in the spore coat of spores for the cotC-lacZ fusion strain.

The pH-activity curves for native and immobilized β-galactosidase are also superimposable from pH 6.0–9.2. At lower pH values, the immobilized enzyme is relatively less active (FIG. 4). FIG. 4 diagrams pH-activity profiles for native β-galactosidase fusion in the spore coat of spores from the cotC-lacZ fusion strain (□) versus native β-galactosidase (●). Buffers employed were 4-morpholine-ethanesulfonic acid (Mes), pH 3.9–6.0, phosphate, pH 6.0–7.5, 4-(2-hydroxyethyl)-1-piperazine-ethanesulfonic acid, (Hepes) pH 6.7–7.2, and N,N-bis(2-hydroxyethyl)-glycine (Bicine), pH 8.0–9.2. All buffers were 50 mM final concentration in the assay mixture. Other assay reagents were as described above. The two data sets were normalized with respect to each other to give the best fit over the pH 5.5–8.5 region.

Figure 5:
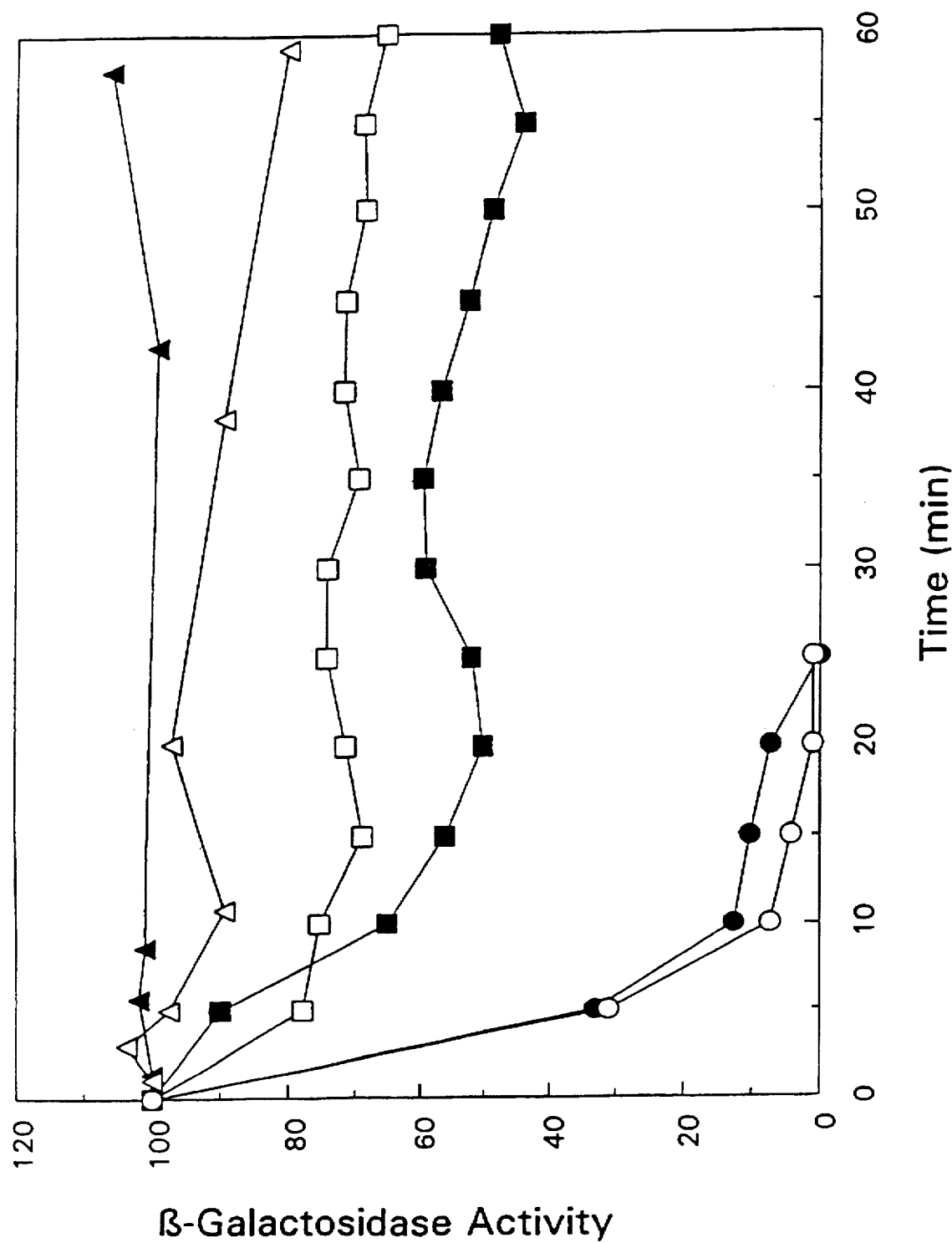
FIG. 5 is a diagram of temperature sensitivity of native β-galactosidase and the CotC-β-galactosidase fusion in the spore coat of spores from the cotC-lacZ fusion. strain.

The sensitivities of native β-galactosidase and CotC:β-galactosidase in the *B. subtilis* spore coat to elevated temperatures are essentially identical (FIG. 5). FIG. 5 diagrams temperature sensitivity of native β-galactosidase (solid data points) and CotC:β-galactosidase fusion (open data points) in the spore coat of spores from the cotC-lacZ fusion strain. Samples of native β-galactosidase or of spores from the cotC-lacZ fusion strain spores were diluted 1–10 into a 0.1M NaHPO₄ buffer, pH 7.5, equilibrated at the indicated temperature. Samples were withdrawn at intervals and chilled on ice, and subsequently assayed for β-galactosidase activity. Data are normalized to 100% activity as measured at t=0. Temperatures tested were 40° C. (Δ), 45° C. (□), and 50° C. (○).

The data above demonstrate that fusions of lacZ with truncated genes encoding *B. subtilis* spore coat proteins are stably incorporated into the surface protein layer of the mature spore. The extent of incorporation, as judged by expressed catalytic activity, varies with the choice of spore coat protein. The cotC-lacZ fusion exhibits more activity than the cotD-lacZ fusion. This might be simply a consequence of a higher level of expression of the cotC-lacZ fusion, or it could reflect the effects of different spore coat environments on fusion protein activity. The gene encoding CotD, cotD, is part of a regulon which is expressed earlier in spore coat formation than is cotC (L. Zheng, et al., supra, 1990). This may imply that CotD is a constituent of the inner layers of the mature spore coat, while CotC is predominantly found in the outer spore coat (J. Errington, supra). Despite this difference in location, both fusion proteins are accessible to substrate.

Native β-galactosidase is a tetramer of 116 kDa subunits (U. Karlsson, et al., *J. Ultrastruct. Res.* 10:457–469, 1964); the cotC segment of the fusion encodes a protein of approximately 5% of the size of β-galactosidase. Apparently, the task of folding and assembling this large protein and inserting it into the spore coat can be successfully accomplished in the course of normal spore development even when the vast majority of the protein to be expressed is of foreign origin. Some, but not all, spore coat proteins can be individually deleted from the genome without gross changes in spore phenotype (L. Zheng, et al., supra, 1988; W. Donovan, et al., supra). The present invention demonstrates that substantial additions to the complement of spore coat proteins can also be successfully integrated into the spore coat.

An order-of-magnitude estimate of the efficiency of the insertion process can be obtained by assuming that the fusion protein has the same molar specific activity as native galactosidase, in which case each spore from the cotC-lacZ fusion strain bears $1.0 \times 10^4$ molecules of β-galactosidase. Taking an estimate of the size of the β-galactosidase from electron microscopy (U. Karlsson, et al., supra), each molecule subtends an area of $8 \times 10^{-17}$ m², and the total area covered by β-galactosidase is approximately $8 \times 10^{-13}$ m². A *B. subtilis* spore is somewhat ellipsoidal, with a major axis of approximately 500 nm (Y. Fujita, et al., *Microbiol. Immunol.* 33:391–401, 1989). The surface area of a geometric form of this size is approximately $3 \times 10^{-13}$ m². Thus, the β-galactosidase molecules occupy an area roughly 3-fold larger than the minimum estimate for the spore surface area. The surface of the spore is a multilayered macromolecular assembly (Aronson, et al., *Bacteriol. Rev.* 40:360–402, 1976); the present calculation confirms that the spore presents a highly elaborated surface to its environment.

Despite this extensive modification of the spore coat, spores bearing β-galactosidase fusions are stable to long-term storage and possess spore coats which still confer lysozyme resistance. Mutant spores in which coat synthesis or assembly is defective frequently manifest a lysozyme sensitive phenotype (Aronson, et al., supra, 1976), so this is an important test of the integrity of the coat bearing these fusions.

The catalytic properties of the immobilized β-galactosidase fusion protein closely resemble those of the native enzyme. Evidently active site structure and overall protein stability are not compromised either by the presence of the amino terminal residues from CotC or by the process of insertion in the spore coat.

The fact that β-galactosidase does not appear to interact strongly with mature wild-type spores suggests that integration occurs as a part of the normal developmental cycle of sporulation, and is not dependent on the particular properties of the protein to be expressed. This gives us reason to believe that the same strategy can be applied for the expression and immobilization of other proteins of interest.

The methodology we have identified for expression and immobilization of β-galactosidase in the spore coat provides a general method for purification of an expressed protein as a component of the spore, without the need to separate it by conventional protein purification techniques. In addition to facilitating purification of proteins, this method provides a route to applications where the expressed protein can be usefully employed in immobilized form. This could serve as a significant improvement over the use of wild-type enzymatic activities of fungal spores, which have previously been employed to carry out biotransformations for fine chemical synthesis (C. Vézina, et al., "Transformation of organic compounds by fungal spores," in *The Filamentous Fungi* John Wiley & Sons, Inc., New York 1(9):158–192, 1974), as the spore can be appropriately engineered for the desired biotransformation.

EXAMPLE 3

Purification of β-galactosidase Linked to Sporulated *B. Subtilis*

The following is envisioned to be a typical method of purifying the enzyme-linked spore coats: One would isolate spores from culture medium by centrifugation at 10,000×g from 5 minutes and then remove the supernatant. The pellet would be resuspended in 10× volume of an aqueous solution of 2% Triton X-100 and 0.2M NaCl and centrifuged again at 10,000×g for 5 minutes. The supernatant would be removed. The resuspension, centrifugation and supernatant removal would be repeated with the following successive wash solutions: once more with aqueous 2% triton X-100

EXAMPLE 4
Isolation of Enzyme by Protease

The following represents a proposed method for isolating an enzyme from the attached spore coat by use of a protease: One would typically first resuspend washed spores in an aqueous solution of 25 mM Tris-Cl, pH 8.0 containing 0.1 mg/ml trypsin and then incubate the suspension for 1 hour at 24° C.–26° C. The suspension would be centrifuged, for example at 10,000×g for 5 minutes, to remove the spores. The supernatant after centrifugation contains the soluble form of the desired enzyme.

This protocol presumes that the desired enzyme is cleaved from the coat protein support by trypsin at the indicated concentration and that trypsin has no deleterious effect on the desired properties of the enzyme. Those skilled in the art can readily devise alternative treatments involving different buffers, different proteases, and different reaction conditions suitable for the production of the soluble forms of different enzymes.

The above paragraph describes a hypothetical example; our constructs described in the Examples above are not suitable for such a protease treatment. (This statement also applies to Examples 5–8 below.)

EXAMPLE 5
Preparation of a Genetic Construct Encoding a Fusion Protein for a Glycosylated Enzyme A genetic construct suitable for expression of a fusion protein in yeast could be created by first identifying by reverse genetics a suitable yeast ascospore coat protein. This could be accomplished by isolation of yeast ascospores (A. Hartig, et al., *Curr. Genet.* 4:29–36, 1981). Ascospore isolation is accomplished by growth of one of many suitable strains of yeast (strain AP-3 is an example) (A. Hartig, et al., supra) at 29° C.–31° C. in 0.5% glucose and 1% yeast extract overnight, then diluting 1:1 with media composed of 0.3% glucose and 1% yeast extract. After 2 hours of further growth at 29° C.–31° C., the cells were harvested by centrifugation at 3,000×g for 5 minutes, washed in water, and resuspended in 1% potassium acetate and grown with shaking at 29° C.–31° C. for 48–72 hours. The resulting spores were collected by centrifugation and treated with mercaptoethanol and glusulase. The spore tetrads were disrupted by glass bead homogenization in 0.5% Triton X-100, and layered on a 75%–90% Percoll, 0.25M saccharose gradient. Spores were collected from the pellet after centrifugation for 1 hour at 10,000 rpm in a Beckman SS-34 rotor (or equivalent). Purification of ascospore walls (P. Briza, et al., *J. Biol. Chem.* 261:4288–4294, 1986) can be accomplished by disruption by homogenization of ascospores purified as described above in the presence of glass beads followed by centrifugation at 3,000×g. The pellet is suspended in an aqueous solution of 60% Percoll and 2% Triton X-100 and centrifuged at 23,000 rpm in a Beckman SW 25.2 rotor or equivalent for 1 hour. The ascospore wall layer is removed and washed by repeated centrifugation in water.

The ascospore walls would be solubilized by an appropriate treatment, such as a combination of reducing agent and strong detergent (e.g., 100 mM dithiothreitol and 1% sodium dodecyl sulfate). The solubilized proteins would be purified using methods known to practitioners of the art, such as polyacrylamide gel electrophoresis, followed by identification of purified proteins from the polyacrylamide gel by staining the gel using one of a number of available methods, such as Coomassie Blue staining, and elution of the bands from the gel. A representative method of accomplishing elution would be electroelution with transfer to a polyvinylidene difluoride (PVDF) membrane. The membrane would then be subjected to automated Edman degradation or other method of determining a portion of its amino acid sequence. From this amino acid sequence, a deduced nucleotide sequence could be inferred, and appropriate oligonucleotides synthesized based on the inferred sequence. These oligonucleotides would then be used to identify the gene associated with the ascospore coat gene product. This could be accomplished in a number of ways familiar to practitioners of the art, including screening of a yeast cDNA library by using the synthetic oligonucleotides as a probe, or by PCR techniques. It would then be necessary to isolate the genomic copy of the gene, identify its promoters and intron sequences, and insert the appropriate sequence into an expression vector suitable for use in the desired strain of yeast. Appropriate expression vectors are well known (F. M. Ausubel, et al., *"Current Protocols in Molecular Biology"*, John Wiley & Sons, New York Vol. 2, Chapter 13, 1994).

EXAMPLE 6
Insertion of Genetic Construct Into Yeast Cells

Transformation with lithium acetate (F. M. Ausubel, et al., *"Current Protocols in Molecular Biology"*, John Wiley & Sons, New York Vol. 2, Chapter 13, 1994). Yeast are grown from an inoculum density of $3\times10^6$ cells/ml to a density of $1–2\times10^7$ cells/ml in 50 ml in a medium consisting of 2% glucose, 2% peptone and 1% yeast extract at 29° C.–31° C. yeast are harvested by centrifugation at 1,100×g for 10 minutes. The pellet is resuspended in 10 ml of an aqueous solution of 10 mM Tris-Cl, 1 mM ethylenediamine tetraacetic acid, pH 8.0. The suspension is centrifuged at 1,1000×g for 10 minutes and the pellet resuspended 10 ml of an aqueous solution of 10 mM lithium acetate. After centrifugation at 1,100×g for 10 minutes, the pellet is resuspended in 0.5 ml of an aqueous solution of 10 mM lithium acetate. The suspension is incubated with gentle shaking (50 rpm) for 1 hour at 29° C.–31° C. Transformation is accomplished by mixing 0.1 ml of the suspension with $1–5\times10^6$ gm donor DNA plus $2\times10^5$ gm carrier DNA (sheared calf thymus DNA or *E. coli* DNA). The suspension is then incubated for 30 minutes at 29° C.–31° C. Add 0.7 ml 40% w/v polyethylene glycol 3350, 0.1M lithium acetate, 10 mM Tris-Cl, 1 mM ethylenediamine tetraacetic acid, pH 8.0 and incubate 45 minutes at 29° C.–31° C., then at 42° C. for 5 minutes. Plate 0.2 ml of the solution on appropriate selective plates (for example, CM -ura plates with yeast strain YEp24). The transformed cells will be able to grow on the selective medium.

EXAMPLE 7
Production and Purification of Glycosylated Enzyme

Yeast ascospores can be prepared in pure form by the methods described above for the preparation of pure ascospores, as described in Example 5.

EXAMPLE 8
Isolation of Glycosylated Enzyme

Glycosylated enzyme could be removed from purified ascospores by chemical or enzymatic treatments as described in Example 4.

It will be readily apparent to those skilled in the art that a number of modifications and changes can be made without departing from the spirit and scope of the invention. Therefore, it is intended that the scope of the invention be restricted only by the claims.

We claim:

1. A method of producing and purifying an enzyme which comprises
   selecting a suitable spore-forming *B. subtilis;*
   forming a genetic construct encoding a protein, wherein the genetic construct comprises a first portion encoding a desired target enzyme and truncated *B. subtilis* spore coat protein which, when transcribed and translated, expresses a fusion protein between the spore coat protein and the target enzyme, and a second portion comprising a DNA sequence causing the transcription of the DNA encoding the desired enzyme during sporulation of the organism,
   transforming the *B. subtilis* with said genetic construct;
   culturing the transformed organism under sporulating conditions wherein spores are formed which have the fusion protein integrally associated with the spore coat; and
   removing undesired impurities from the spore bearing the spore coat-fusion protein combination.

2. A method of claim 1 in which the enzyme is isolated from the host organism by use of a cleaving agent which severs the attachment between the spore coat and the enzyme.

3. The method of claim 1 wherein the attachment is a covalent bond.

4. A method of claim 1 in which the enzyme is β-galactosidase.

5. An immobilized enzyme preparation comprising the spores of a host organism with an enzyme integrally associated which has been prepared by the method of claim 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 602 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AAGCTTCACA  AAAATACTCG  TTATTTTGTT  TGTGGGTTTT  TTAGTATTTG  GGCCTGATAA     60
ACTGCCGGCG  CTTGGCCGTG  CAGCAGGAAA  AGCCTTATCA  GAATTTAAAC  AAGCAACAAG    120
CGGACTGACT  CAGGATATCA  GAAAAAATGA  CTCAGAAAAC  AAAGAAGACA  AACAAATGTA    180
GGATAAATCG  TTTGGGCCGA  TGAAAAATCG  GCTCTTTATT  TTGATTTGTT  TTTGTGTCAT    240
CTGTCTTTTT  CTATCATTTG  GACAGCCCTT  TTTTCCTTCT  ATGATTTAA   CTGTCCAAGC    300
CGCAAAATCT  ACTCGCCGTA  TAATAAAGCG  TAGTAAAAAT  AAAGGAGGAG  TATATATGGG    360
TTATTACAAA  AAATACAAAG  AAGAGTATTA  TACGGTCAAA  AAAACGTATT  ATAAGAAGTA    420
TTACGAATAT  GATAAAAAAG  ATTATGACTG  TGATTACGAC  AAAAAATATG  ATGACTATGA    480
TAAAAAATAT  TATGATCACG  ATAAAAAAGA  CTATGATTAT  GTTGTAGAGT  ATAAAAAGCA    540
TAAAAAACAC  TACTAAACGC  CATTAACAAA  AGCATAAAAA  ACACTACTAA  ACGCCATTAA    600
CA                                                                       602
```

( 2 ) INFORMATION FOR SEQ ID NO:2:

( i ) SEQUENCE CHARACTERISTICS:
        ( A ) LENGTH: 249 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
TTATGGAAAG  GGGATTTTAT  CATGCATCAC  TGCAGACCGC  ATATGATGGC  GCCAATTGTC     60
CATCCTACTC  ATTGCTGTGA  ACACCATACG  TTTTCGAAGA  CTATCGTGCC  GCACATTCAC    120
CCACAGCATA  CAACAAACGT  AAACCACCAG  CATTTTCAGC  ACGTTCACTA  CTTTCCACAC    180
ACTTTCTCAA  ATGTTGACCC  GGCTACGCAT  CAGCATTTTC  AAGCAGGAAA  ACCTTGCTGC    240
GACTACTAG                                                                249
```

( 2 ) INFORMATION FOR SEQ ID NO:3:

( i ) SEQUENCE CHARACTERISTICS:
        ( A ) LENGTH: 2306 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GGCGCCTTAA  GGGACCTTCT  ATGACAAATA  TGGTGAGGTA  TGCAACCTCA  ATGAAGAGCA     60
```

-continued

| | | | | | |
|---|---|---|---|---|---|
| ATGAGAAAAT | TTAAGGGGTA | AGTAAGCATC | GGAATTTGTT | GTTTCCTAAC | AATTTGTCTA | 120 |
| ATTTACTCAA | TAATATCAGG | AGAATTGATC | GAAAAAAGCA | AACCAGGAAC | CCCTCACAAA | 180 |
| TAAGGGAACA | TAAAGTAATT | GCTCGTCTTT | ACATACATGG | CACTCAATCC | CAGACGTCGC | 240 |
| GTGCTAAAAA | TCCTTATATT | ATTGGCCCCT | CAGGAGTTTA | TTTGAATTTT | GATTGCATTG | 300 |
| CTTTCAGTGG | ACAGTATATC | ATAAAATTTG | CAAGGGCATA | GTGCCTGCCC | TACGATGTTG | 360 |
| TAAAACAATT | TCTGAAAATA | GGTTCAGAAT | CAAAAATGAT | GTATAAATAT | TGAAATAAAT | 420 |
| TTTCACATAA | ATTGTGCTCC | TCCGCAAAGT | CTTGACTAAA | TAAACAATTT | GTTAATATCC | 480 |
| TAATTCGGTA | AAGCTTTGTC | GAGACATTAA | CAAAAATGAC | ATTACTAGC | AACTTGCCCT | 540 |
| CAAGCTCCGA | GCAGTCAATA | TCACCACCTG | CCTCTTCATT | TTCTTCATCG | ACTGATACGT | 600 |
| TGAAAGATAT | TGATATTCCC | CATAATGGGG | CCGATTTGTC | TACATATAGT | AAATTTCTGG | 660 |
| CCCTGTATTG | CAGAAGCGAC | AAATGTGACG | ATTTTACTC | TTTAGAGGAA | AAACAGAATT | 720 |
| GTAAATTTGG | AGACCAATGG | CTCGACTTTA | TCAACACTAT | TCACAATCTG | GACTTTCTG | 780 |
| AATCCGAAGT | AAGTGGACGG | GTTCTGAAA | GAATTTTGCC | AGCTTCTTTA | GCAAATAAAT | 840 |
| TTACCAATAA | TTTAGGAGTG | GCAATAAAGA | TTTCTGAATA | TACACGCGAT | GACGAACGCC | 900 |
| AGATTCGTGG | GTGTGTTACA | ACAGTTGAGA | ATGAAAATTC | TTTCAATAAC | TGGTTCGTAT | 960 |
| ATCATATTTT | AGACCAATCT | CAATTATCTC | TAAGTGAACA | TCCAATTGTA | ACCAAGAAG | 1020 |
| TTAAGTATCA | CGAATTATTT | GCAGATTTTT | TTGAGAAAAA | TTTGAAAAAC | ACAATAGTTA | 1080 |
| ATGATCAATG | GAATTTTGGT | GGCCGTGATT | ATTTTATTGA | ACGTTCAAGA | TATTTTACCG | 1140 |
| ATCGATATTT | GAGAATTGAA | TGCATCTTGC | CAGCGTTCC | ATGTAAGTCA | TCTAATGAGC | 1200 |
| AAAAAGTGTA | CGGTTCCGTT | CCTGACAAAG | GCGAAGAACT | CGCTTTGAAA | AGATTAATAA | 1260 |
| AAGCCACACA | AGACCTTGTC | AAGATATATC | CACCGGGTAT | GAAAATTTGG | ATAGTTAGTG | 1320 |
| ATGGCCATGT | TTCCTCCGAT | TGTATTGGGG | TCGATGATGA | CGTCGTGAGT | ACTTACACGA | 1380 |
| CCAAATTGCA | CGAACTGTAT | AAAAGAGTGG | CTATACCTGG | TGTTGACGCC | ATTGGCTTTT | 1440 |
| GTGGATTGAA | CGATTTATTT | TTTAGCGGTG | CAGCTAGTAA | AGTTTCGAT | CCAAAGTGGG | 1500 |
| TTAGTGATGT | TGAAGTTGCA | CACTACACAG | GAACTCAAAT | CTGTCCTAAG | TCCGATTTGT | 1560 |
| CGAGACAGAT | TTTGATGAAA | GGCTGTGATA | CAGATGCAGG | TCGTTTGAGA | AAGCAGATTG | 1620 |
| CAATAGAAGG | ACATCCAAGA | TTGCATCTGT | ATAGGGGCTT | TCACGTTTT | ATGATGGAAG | 1680 |
| ATTTATCTCT | ACTGGAACAT | TTCCAAAGTT | ATTCCAGAAA | AAAATTCAAG | AAAATCATTT | 1740 |
| CAATGATCGC | TTTTAACATG | ATTAAGAGAA | ATGACGCGTA | TTCGAACTTA | GTGGAATTGA | 1800 |
| TATTCCCTCA | TCATTTGAGA | ATTTCTATTC | ATGCGCACAC | TAACAGCGGG | CCCAAATTTG | 1860 |
| GTATAAAAGT | AATCTCCAAC | GAACAGTGTT | CTATTGTTAG | TTCGTTAGAA | GACCTTGATG | 1920 |
| AACCCAAATT | TGAAGATTTT | TTACATATTC | CCACACCTTG | GCATAATTGT | GTCGTGAAGG | 1980 |
| TTGAGGATGA | AAAGGAGAAA | TACTTTTTGA | CAAAATCAAA | AGTAGTCAAG | GAGGCTCTCG | 2040 |
| AAAAGGGTAT | GTATGATGGT | GTATGGAAAG | ATACTCGTTT | CGATATTGGA | GAAGGAGGAC | 2100 |
| ATTCGTTAT | CAAGAAAATC | TCTTAATAAA | GTAAGAGCGC | TACATTGGTC | TACCTTTTTG | 2160 |
| TTCTTTTACT | TAAACATTAG | TTAGTTCGTT | TTCTTTTTCT | CATTTTTAT | GTTTCCCCCC | 2220 |
| AAAGTTCTGA | TTTTATAATA | TTTTATTTCA | CACAATTCCA | TTAACAGAG | GGGAATAGAT | 2280 |
| TCTTTAGCTT | AGAAAATTAC | TGATCC | | | | 2306 |

( 2 ) INFORMATION FOR SEQ ID NO:4:

( i ) SEQUENCE CHARACTERISTICS:

(A) LENGTH: 45 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:4:

| Met | Gly | Tyr | Tyr | Lys | Lys | Tyr | Lys | Glu | Glu | Tyr | Tyr | Thr | Val | Lys | Lys |
|---|---|---|---|---|---|---|---|---|---|---|---|---|---|---|---|
| 1 | | | | 5 | | | | | 10 | | | | | 15 | |

| Thr | Tyr | Tyr | Lys | Lys | Tyr | Tyr | Glu | Tyr | Asp | Lys | Lys | Asp | Tyr | Asp | Cys |
|---|---|---|---|---|---|---|---|---|---|---|---|---|---|---|---|
| | | | 20 | | | | | 25 | | | | | 30 | | |

| Asp | Tyr | Asp | Lys | Lys | Tyr | Asp | Asp | Tyr | Asp | Lys | Lys | Tyr |
|---|---|---|---|---|---|---|---|---|---|---|---|---|
| | | 35 | | | | | 40 | | | | | 45 |